(12) United States Patent
Lalezari

(10) Patent No.: US 7,919,266 B2
(45) Date of Patent: Apr. 5, 2011

(54) METHOD OF DETECTING RED CELL ANTIGEN-ANTIBODY REACTIONS

(75) Inventor: Parviz Lalezari, Scarsdale, NY (US)

(73) Assignee: Clavina Diagnostics, Inc., Longwood, FL (US)

( * ) Notice: Subject to any disclaimer, the term of this patent is extended or adjusted under 35 U.S.C. 154(b) by 240 days.

(21) Appl. No.: 12/148,946

(22) Filed: Apr. 23, 2008

(65) Prior Publication Data

US 2008/0261248 A1    Oct. 23, 2008

Related U.S. Application Data

(60) Provisional application No. 60/925,730, filed on Apr. 23, 2007.

(51) Int. Cl.
*G01N 33/00* (2006.01)
*G01N 31/00* (2006.01)
*G01N 33/539* (2006.01)

(52) U.S. Cl. ........ 435/7.25; 435/2; 435/287.2; 436/506; 436/507; 436/513; 436/518; 436/520; 436/538; 436/539; 436/17; 436/18; 436/165; 436/166; 436/175; 436/177; 436/178; 436/179

(58) Field of Classification Search ............... 435/2, 3, 435/7.25, 40.51, 286.1, 286.7, 287.2, 288.6; 436/506, 513, 518, 520, 523, 524, 527, 528, 436/535, 538, 539, 17, 18, 63, 165, 175, 177, 178, 179, 166

See application file for complete search history.

(56) References Cited

U.S. PATENT DOCUMENTS

| 4,436,825 | A  | * | 3/1984  | Lalezari ....................... 435/7.25 |
| 2007/0298446 | A1 | * | 12/2007 | Malyska et al. ............. 435/7.25 |

OTHER PUBLICATIONS

British Journal of Experimental Pathology, Vo. 26, pp. 255-266 (1945).

* cited by examiner

*Primary Examiner* — Gailene R Gabel
(74) *Attorney, Agent, or Firm* — Hedman & Costigan, P.C.; James V. Costigan

(57) ABSTRACT

A process for the detection of antibodies in a test sample by preparing a suspension of erythrocytes with a test serum or plasma by mixing a test serum or plasma with erythrocytes; incubating the suspension of erythrocytes at a temperature of from 37° C. to 45° C. to bind any antibodies in the test serum or plasma to the surface of said erythrocytes; combining the suspension of erythrocytes with an amount of a solution of a macromolecule which is effective to agglutinate the erythrocytes; packing the resultant red cell agglutinates by centrifuging the suspension of erythrocytes; and, determining the presence of anti-erythrocyte antibodies by observing if antibody-dependent erythrocyte agglutination has occurred.

9 Claims, No Drawings

METHOD OF DETECTING RED CELL ANTIGEN-ANTIBODY REACTIONS

This application claims the benefit of provisional application Ser. No. 60/925,730, filed Apr. 23, 2007.

BACKGROUND OF THE INVENTION

Numerous techniques for the detection of antibodies exist. These are utilized in many applications to determine the presence of any, or given, antibodies and to measure their concentration in a variety of fluids, most particularly blood. These techniques are particularly useful for typing erythrocytes and in the cross-matching of blood for transfusion.

The main technique commonly used in blood banking is called the antiglobulin test (AGT) which is performed by incubating a serum or plasma which is being tested for the presence of an antibody, with a suspension of the red blood cells for 30 minutes at 37° C. This phase is required to allow the binding of the antibodies, if present in the test serum, to the red cells. In the second phase, the sensitized red cells are washed three times with an isotonic solution of sodium chloride to remove the free serum proteins including free immunoglobulins. In the final phase, the washed red cells are mixed with a solution of antibody against human immunoglobulins, centrifuged and the red cell pellets are examined for aggregation, which would result from the reaction of the antiglobulin reagent with the red cell-bound antibodies, if present. For red cell typing, the same procedure is followed except that the test red cells are incubated with a known antibody used for typing. The completion of the AGT requires a total of 35 to 45 minutes, a time that is unacceptable for emergency situations Another test commonly used is The Manual Polybrene Test (MPT) which is rapid, simple and economical. The processes involved can be divided into three phases, Namely the Sensitization Phase in which the antigen-antibody reaction takes place in a low ionic medium (LIM); the Polybrene-induced aggregation phase in which the sensitized erythrocytes are non-specifically aggregated by Polybrene, a positively charged synthetic polymer, and the Polybrene-Neutralization Phase in which a salt such as trisodium citrate is used to disperse the aggregates produced by polybrene. The occurrence of an antigen-antibody reaction is recognized by persistence of agglutination after the Polybrene effects have been reversed. Although the MPT is more sensitive than other existing tests for detection of many erythrocyte antibodies, it has been found to lack adequate sensitivity for Kell-related antibodies, a deficiency that has prevented MPT from becoming a universal blood bank test in the countries and populations where Kell-incompatibility is relatively common. This invention describes a new procedure which, unlike the AGT, is rapid, does not require red cell washing after red cell sensitization, and unlike the MPT, is highly sensitive for detection of the Kell related and other antibodies. The most commonly employed prior art procedure based on the use of antiglobulin reagent is described in U.S. Pat. No. 4,436,825. The antiglobulin procedure is described in an article by Coombs et al at Vol. 26, page 255 of the Brit. J. Exp. Path (1945). These procedures, however, have the drawbacks of being time-consuming and of inadequate sensitivity.

Another method is an automated method described in an article in Transfusion, Vol. 8, No. 6 November-December 1968 by P. Lalezari. That method utilizes another approach, however, that method has substantial drawbacks. It involves careful attention to proportions of ingredients and reagents as well as complicated equipment. Further, it too is time-consuming.

The disclosures of these articles are incorporated herein by reference. The drawbacks of these existing techniques pose substantial impediments to the need for fast and simple antibody detection with acceptable accuracy. The need for improved antibody detection techniques is therefore clear.

The new test is based on the discovery that macromolecules which are water soluble polymers when used in an amount that potentiates the agglutination of erythrocytes in the presence of antibodies or erythrocytes coated with antibodies. The macromolecules include sodium salts of various polycarboxylic acid macromolecules (hereafter PCA) such as poly[(isobutylene-alt-maleic acid)$NH_4$-co(isobutylene-alt-maleic anhydride)] (hereafter "PIMA)"; various polyacrylic acids (PAA), carboxymethyl celluloses (CMC), polyvinyl pyrrolidone (PVP), and polymers of negatively charged amino acids (polyglutamic acid) of appropriate molecular sizes will react with immunoglobulins and will cause the immunoglobulins to precipitate. It has also been found that 2-hydroxyethyl cellulose with a weight average molecular weight of 90,000 Dalton is effective as a macromolecule at a concentration of this molecule was 0.75 w/v % in 2.5 w/v % dextrose. Another example of a macromolecule is hydroxypropyl cellulose with a weight average MW of 80,000 Dalton. The effective concentration of this molecule was between 2 to 3 w/v % in 2.5 w/v % dextrose. At these concentrations, these molecules potentiated the reaction of "complete" anti-M and anti-Kell antibodies. Other useful neutral macromolecules include Ficoll 400, Dextran T70, methyl cellulose (producing about 4,000 cP viscosity at 2% solution in water) and the like. These macromolecules when used at low concentrations with dilute systems did not cause red cell aggregation but caused the antibody-dependent red cell agglutinations produced by undiluted antibodies to become stronger and more stable. Examples of this type of effects are seen with polyethylene glycols (PEG) with weight average molecular weights of 8,000 and 20,000 Daltons. When these PEGs are used at concentrations between 5 to 10 w/v %, they stabilize the reaction of undiluted anti-M or anti Kell antibodies as used in Example I but they do not potentiate the reaction with diluted antibodies.

Neutral macromolecules such as 2-Hydroxyethyl cellulose and hydroxypropyl cellulose may be used at concentrations of 5 to 10% w/v slightly potentiate the reaction of warm antibodies as described herein but they are much less effective as compared to PCA or PVP.

If erythrocytes are coated with anti-erythrocyte antibodies, the addition of an effective amount of these molecules will cause the erythrocytes also to aggregate. It has also been discovered that polyvinylpyrrolidones (PVP) of appropriate molecular sizes also react with red cell-bound antibodies and cause their aggregation. The reactivity of large PVP molecules is suggested to be due to their weak positive charge which binds to the negatively charged moieties on immunoglobulin molecules. In this invention, the need for washing the sensitized red cells, as required in the standard antiglobulin test, is eliminated because the amount of effective macromolecules used are in excess of what may be neutralized by the proteins in the test plasmas. The PCA and PVP induced aggregation of erythrocytes which have antibodies bound to the surface, may be used as a test for the presence of anti-erythrocyte antibodies in a sample of serum or plasma, or for red cell typing. These tests are widely used in blood banks for red cell typing, for detection of anti-erythrocyte antibodies in collected whole blood, for cross-matching prior to the release of whole blood for transfusion or for the preparation of blood derived products.

By virtue of their ability to create a viscous environment, macromolecules are known to cause a reversible and nonspecific red cell aggregation known as rouleaux formation. In previous art, PVP was used as a rouleaux forming agent, to replace centrifugation, in a continuous flow system (Sturgeon et al. Vox Sang. 8:438, 1963). The ability to act as an antiglobulin agent described in this invention, however, is the newly recognized property of the PVP molecule. Neutral macromolecules such as polyethyleneglycols cause rouleaux formation but unlike PCA or PVP do not have antiglobulin activity.

SUMMARY OF THE INVENTION

A process for the detection of antibodies in a test sample containing serum or plasma, said process comprising:
(a) preparing a suspension of erythrocytes with a test serum or plasma by mixing a test serum or plasma with erythrocytes;
(b) incubating the suspension formed in step (a) at an ambient temperature, e.g. 18° C. to 45° C. for a period of time from sixty seconds to 10 minutes to bind any antibodies in the test serum or plasma to the surface of said erythrocytes
(c) combining said suspension with an amount of a solution of a macromolecule which is a water soluble polymer which potentiates the agglutination of erythrocytes in the presence of antibodies or erythrocytes that are coated antibodies;
(d) centrifuging the combined red cell-serum-PCA or -PVP suspension to create a pellet of the red cells;
(e) determining the presence of anti-erythrocyte antibodies by observing if erythrocyte aggregation remains after gentle agitation of the red cell pellets
(f) in an alternative procedure, the red cell pellet is re-incubated for an additional 5 to 10 minutes and then examined for persistence of red cell agglutination. This second incubation has been found to increase the test sensitivity.

Whereas, the process has been described as "comprising" the recited steps, the invention also includes a process where the invention "consists essentially of" in that it includes the steps recited above without the inclusion of a step that has a material effect on the process.

The persistence of agglutination indicates the presence of an antibody against the test erythrocytes. In accordance with standard laboratory practice, a control is usually run in which the test serum or plasma is replaced by a normal serum or plasma The effective concentration of PCA or PVP is the level that supports antibody detection but its rouleaux forming effects is readily reversed in the control serum or plasma.

The process of the invention also includes a format in which the suspension of erythrocytes in test serum or plasma described in step (a) above are combined with the PCA or PVP solutions and incubated together as in step (b).

The process of the invention also includes the optional steps of incubating the red cells and serum or plasma in step (b) above with a monosaccharide such as sucrose, fructose, dextrose or the like at a concentration of 0.25-5 wt/v % of monosaccharide in water. In the presence of the monosaccharide, the antibody uptake by the red cells is noticeably increased and thus it makes the test more sensitive to situations involving a low titer of antibodies.

The process of the invention also includes the optional steps of incubating the red cells and serum or plasma in step (b) above with a solution of a neutral amino acid such as glycine to provide a low ionic isotonic medium to enhance antibody uptake by the test red cells.

The isotonic-low ionic medium may be composed by a mixture of the sugar and the amino acids described above.

The process of the invention also includes the optional step of adding a salt to the PCA or PVP solutions used in step (c) above that will help dispersion of the rouleaux formation, which results from the presence of macromolecules. An amount of any such salt will be added that is sufficient to help dispersion of the rouleaux formation. The salts found to be useful include trisodium citrate, and ammonium salts.

If an ammonium salt is added to PCA or PVP, the ammonium salt concentration may be at 0.0025 to 0.2 molar concentrations. Suitable ammonium salts such as ammonium chloride, ammonium acetate, ammonium sulfate, ammonium citrate and the like may be added to the macromolecule solutions.

The invention also includes a kit for use in the detection of antibodies, wherein the kit comprises:
(a) an aqueous solution of a macromolecule such as a polycarboxylic acid salt or PVP, in concentrations which are effective for antibody detection; and optionally;
(b) an aqueous diluent for erythrocytes and the test serum or plasma; and/or
(c) an aqueous solution of a monosaccharide, a neutral amino acid or a combination thereof, at a concentration which is effective to enhance the sensitivity of the test; and/or;
(d) a solution of the said macromolecules which also contain effective concentrations of a salt which facilitates dispersion of red cell rouleaux.

The concentration of the aqueous PCAs, or PVP solutions may vary from 0.05 to 5 w/v %.

This test produces accurate results which are substantially independent of most variations in the amount or type of ingredients and reactants employed.

DETAILED DESCRIPTION OF THE INVENTION

The process may be completed in mere minutes with simple laboratory equipment. The present process is suitable for detection of antibodies in any normally aqueous sample. Most commonly, it is applied to a blood serum or plasma (including derivatives thereof). An important application is the use of this technology to potentiate commercially available red cell typing reagents. Erythrocytes are added to the test sample after an optional washing step with isotonic salt solution. Desirably the sample contains from 0.5 to 3% more preferably 1% to 2%, suspended erythrocytes (or antigen coated erythrocytes) by total volume. These erythrocytes are normally obtained from a different source donor to ensure that they will accept any antibodies present in the sample.

In the case of cross-matching blood for transfusion, the red cells are from normal blood donors.

Erythrocytes may be obtained from the same donor as the serum if the presence of an autoantibody is being sought.

The preferred polymers of polycarboxylic acids are:
(a) polymer of [(isobutylene-alt-maleic acid)$NH_4$-co-(isobutylene-alt-maleic anhydride)] (PIMA) with an average molecular weight of 60,000 Dalton although PIMA having differing molecular weights may be utilized;
(b) sodium salts of polyacrylic acids (PAA) ranging from 15,000 to 3 million Dalton. The preferred molecule is the PAA with a weight average MW of 240,000 Daltons;
(c) poly(methacrylic acid Na) with a weight average MW of 9500 Daltons; and
(d) sodium salts of carboxymethylcellulose with low viscosity grade.

The preferred PVP will be of varying molecular weights, but the preferred PVPs will have a weight average molecular weight of 360,000-1.3.million Daltons.

The incubation of the erythrocytes and the test serum or plasma, before addition of the macromolecules or in combination with the desired polymers, with or without an additional low ionic-isotonic solution such as normal saline, may be carried out at a temperature of from 18° C. to 45° C. for a period of time from sixty seconds to 10 minutes. For example, incubation may be carried for 3 to 10 minutes, preferably for 5 minutes at ambient temperature or 37° C., or for 2-5 minutes at 40° C. to 45° C. Alternatively, the incubation may be carried out at 39° C. for 5 minutes. The exact temperature and time is not critical provided that the incubation is carried out for a sufficient time and at a sufficient temperature to cause adequate anti-erythrocyte antibodies to bind to the erythrocytes.

Once the antibody uptake is completed, the cell suspensions are centrifuged for 10 to 60 seconds at 1000×g and the pelletted cells is then gently mixed and examined for residual aggregation. For potentiation of the reaction of the so called "complete" antibodies, such as those used in typing reagents, incubation is not essential and red cell-antibody-polymer mixtures are centrifuged for 10 to 20 seconds. In the absence of antibodies, the red cells rapidly disperse and reassume a suspension or colloidal form. In contrast, the presence of antibody is evidenced by its coupling effect on the erythrocytes. Therefore antibodies are revealed or detected by persistence of the agglutinates within the suspension.

In the absence of any residual agglutination, the suspended cells may be centrifuged again for 15 seconds at 1000×g and incubated for an additional 5 to 10 minutes and then re-examined for agglutination.

These procedures allow detection of antigen-antibody reaction through simple monitoring of the dispersed aggregates. For example, visual monitoring (aided, if desired, by a microscope or a magnifying mirror) allows rapid observation of the degree, if any, to which the agglutinates persist. Such persistent agglutination occurs in inverse relationship to the concentration of antibody in the initial test sample.

This relationship also allows for precise quantitative measurement of antibody concentration. By use of either standardized conditions in the process or duplication utilizing control samples, accurate quantitative analysis is achieved.

As described earlier, the process of this invention may be carried out at different time-temperature combinations, offering multiple options.

Lower temperatures may be advantageous to permit separate detection of cold-reactive antibodies. These known antibodies preserve agglutination only at lower than ambient temperatures. Consequently, they may be detected by pre-incubation of the red cell-antibody-polymer mixtures at about 0° C. to 6° C. prior to centrifugation and monitoring.

Accordingly, this process also allows qualitative detection of antibodies which are cold versus warm reacting antibodies.

The process of the invention may be adapted for use in automated equipment by using any of PCA or PVP solutions as a step in the automated analysis according to the procedures described herein.

The process of this invention will be more fully described and better understood from the following examples.

EXAMPLES

Detection of red cell antibodies described in this invention can be carried out under different conditions based on the properties of the antibodies being tested Example 1

This example represents the test designed for detection of antibodies that usually react at room temperature and are referred to as "complete" antibodies. Examples are antibodies to ABO, MNSs, Lewis, P and the like blood groups. In this format, 0.05 ml or one drop of the red cell suspension, suspended in normal saline at 1% to 3% concentration is mixed with 0.1 ml or two drops of the test serum or plasma, or the typing reagent. To this suspension, 0.1 ml of one of the polymers dissolved in 2.5 w/v % glucose at an effective concentration is added and the mixture is centrifuged for 10 to 20 seconds at 1000×g. The red cell buttons are then examined for agglutination. The test does not require incubation. However sensitivity can be increased if the cell-antibody-polymer combinations are kept for 5 to 10 minutes at ambient temperature before centrifugation. Control similarly treated is a tube which contains the test cells, and the reference cells in cases of cell typing, with normal serum or plasma and the polymer. In the example 1 below, various dilutions of a commercially available anti-M antibody, prepared in a normal plasma were tested with and without addition of a polymer for comparison: The polymer used was PIMA at 0.6 w/v % diluted in 2.5 w/v % dextrose. The test tubes were centrifuged for 15 second at 1000×g without incubation and the results were recorded:

| Dilutions of | Results | |
| --- | --- | --- |
| anti-M | With PIMA | without PIMA |
| Undiluted | 4+ | 4+ |
| 1:10 | 4+ | 3+ |
| 1:50 | 4+ | Negative |
| 1:100 | 4+ | " |
| 1:500 | 3+ | " |
| 1:1,000 | 2+ | " |
| 1:5,000 | 2+ | " |
| 1:10,000 | Negative | " |

The results show more than a one hundred fold increase in the test sensitivity by the addition of PIMA. Identical results were obtained when instead of PIMA either a 2 w/v % solution of PVP (MW 1.3 million Dalton) or 0.5 W/v % of polyacrylic acid Na, both in 2.5% dextrose, were used. In an example of monoclonal anti-Kell antibody, addition of PIMA increased the test sensitivity over 40 fold. Similar results were obtained with monoclonal anti-Rh antibodies and antibodies to Lewis, S, and the like. All other polymers described in this invention at appropriate concentrations adjusted to give a negative reaction with normal plasmas, produced similar results. The reactions detected in the presence of polymers not only were remarkably strong but remained stable whereas in the absence of polymers, the weak aggregates produced by the test material were unstable and dispersed after being kept on the bench.

Example II

For detection of warm-reacting antibodies, the test is modified and is performed in four phases. In the first phase or sensitization phase, 0.05 ml or one drop of the red cell suspension, suspended in normal saline at 1% to 3% concentration is mixed with 0.1 ml or two drops of the test serum or plasma. The combination is incubated for three to 10 minutes, preferably for five minutes at 37 degrees Centigrade. In the second phase, 0.1 ml of an appropriate dilution of PCA or PVP dissolved in normal saline, with 0.005 molar trisodium citrate, dissolved in 5% glucose, is added and the test tube is centrifuged for 15 seconds at 1000×g. Control similarly treated is a tube which contains the test cells with normal serum or plasma. The third phase is recentrifugation for 10-20 seconds and a second incubation of the pellets at 37 degrees for 5 to 10 minutes, preferably for 8 minutes. This re-incubation, optionally used only if no antibody-dependent aggregation is detected in phase 2, increases the test sensitivity because the reaction of the effective polymers with the red cell bound antibodies increases with time. The final phase is evaluation of the results by visual examination of the red cell buttons for agglutination after gentle mixing. In the absence of antibodies (normal control) the red cells readily disperse and the presence of antibodies is indicated by detectable agglutination. The sensitivity of the test can be increased by increasing duration of incubation time; the longer the second incubation time, the higher test sensitivity. Finally, as macromolecules, the effective polymers provide stability to the agglutinates produced in the test.

The PCA and PVP tests have been found to detect all tested anti-Kell antibodies strongly and with stability. In addition, many other antibodies such as anti-Rh(D), Kidd (Jka), Duffy (Fy), M, N, Le, Lu tested have been detected with stronger reactions, as compared to the standard tests. An example of a test, using PIMA at 0.4% concentration simultaneously carried out with a standard AGT, for comparison, is shown below:

| Test | Control | Anti K #1 | Anti K#2 | Anti K #3 | Anti Fy | Anti Rh | Anti Jka |
|------|---------|-----------|----------|-----------|---------|---------|----------|
| PIMA | Negative | 4+ | 4+ | 4+ | 2+ | 3+ | 2+ |
| AGT | Negative | 4+ | 2+ | 1+ | Negative | Trace | Trace |

Method for preparation of PIMA-salt solution: This solution requires a final 2.5 w/v % concentration of glucose, or similar sugars. For unexplained reasons, in the absence of a sugar, the reaction of PIMA is not as strong. To achieve this concentration, a 0.8 w/v % solution of PIMA was made in 0.9 w/w % NaCl and mixed with an equal volume of a 0.01 molar solution of trisodium citrate made in 5 w/v % glucose. The concentration of citrate should preferably be in the range of 0.005 to 0.02 molar.

In the Examples I and II given above, monitoring was performed simply through visual inspection of macroscopic agglutinates. They therefore constituted only negative-positive detection tests. More accurate and quantitative results may be obtained by careful microscopic monitoring involving detection of degree of erythrocyte dissociation. Similar results may be obtained by other techniques including, for example, photometric analysis of the red cell dispersion. This allows precise measurement of degree of dissociation.

For these quantitative processes of the present invention, control samples are often run in tandem with the test sample. This ensures accuracy of detection measurement. Such controls may either possess none or a predetermined amount of antibody according to standard analytical procedures.

In addition to the various reagent constituents previously mentioned, others may be present. These constituents include bactericides, such as sodium azide, to avoid contamination; sugars, such as dextrose, to provide nutrients and sufficient osmotic pressure to ensure normalacy of the erythrocytes; and the like for similar known or apparent purposes.

It is to be understood that these changes may be made in the following exemplary embodiments in the light of the above teachings. Additional modifications and/or variations may also be made without departing from the scope and spirit of the invention which therefore shall be measured by the claims which follow.

What is claimed is:

1. A process for the detection of antibodies in a test sample containing serum or plasma, said process comprising;
    (a) preparing a suspension of erythrocytes with a test serum or plasma by mixing the test serum or plasma with erythrocytes;
    (b) incubating the suspension formed in step (a) at a temperature of from 37° C. to 45° C. for a period of time from sixty seconds to 10 minutes to bind any antibodies in the test serum or plasma to antigens on the surface of said erythrocytes;
    (c) combining said suspension in step (b) with an amount of a solution of a polycarboxylic acid macromolecule which is poly [(isobutylene-alt-maleic acid)NH4-co (isobutylene-alt-maleic anhydride)] (PIMA) used at a concentration of 0.1 to 5 wv % which potentiates the agglutination of said erythrocytes;
    (d) centrifuging the suspension of step (c); and,
    (e) determining the presence of anti-erythrocyte antibodies by detecting for occurrence of erythrocyte agglutination in the suspension.

2. The process of claim 1 wherein the PIMA is used in combination with an ammonium salt.

3. The process of claim 1 wherein the PIMA is used in combination with an ammonium salt and a monosaccharide.

4. The process of claim 1 wherein the PIMA is used in combination with citric acid salt.

5. The process in claim 1 wherein the product of step (c) is incubated for an additional 5 to 10 minutes at 37° C.

6. The process of claim 1 wherein the agglutinated erythrocytes without bound antibody are monitored for dissociation.

7. The process of claim 1 wherein the agglutinated erythrocytes with bound antibody are monitored.

8. The process of claim 1 wherein the antigen is native to the erythrocytes.

9. The process of claim 1 wherein the antigen is artificially coupled to the erythrocytes.

* * * * *